(12) United States Patent
Rea

(10) Patent No.: US 8,103,339 B2
(45) Date of Patent: Jan. 24, 2012

(54) NERVE STIMULATOR WITH SUCTION CAPABILITY

(75) Inventor: James Lee Rea, Ventura, CA (US)

(73) Assignee: Neurovision Medical Products, Inc., Ventura, CA (US)

( * ) Notice: Subject to any disclaimer, the term of this patent is extended or adjusted under 35 U.S.C. 154(b) by 475 days.

(21) Appl. No.: 12/358,179

(22) Filed: Jan. 22, 2009

(65) Prior Publication Data

US 2009/0264944 A1    Oct. 22, 2009

Related U.S. Application Data

(60) Provisional application No. 61/124,890, filed on Apr. 21, 2008.

(51) Int. Cl.
| | |
|---|---|
| *A61B 5/04* | (2006.01) |
| *A61B 5/05* | (2006.01) |
| *A61B 5/00* | (2006.01) |
| *A61B 17/20* | (2006.01) |
| *A61B 18/04* | (2006.01) |
| *A61B 18/18* | (2006.01) |
| *B65D 81/00* | (2006.01) |
| *A61N 1/30* | (2006.01) |

(52) U.S. Cl. .......... 604/20; 600/546; 600/547; 600/554; 600/573; 600/576; 604/21; 604/22; 606/32; 606/41

(58) Field of Classification Search .................. 600/546, 600/547, 554, 573, 576; 604/20–22; 606/32, 606/41
See application file for complete search history.

(56) References Cited

U.S. PATENT DOCUMENTS

| | | | |
|---|---|---|---|
| 2,808,826 A | | 10/1957 | Reiner et al. |
| 4,461,300 A | | 7/1984 | Christensen |
| 4,824,433 A | | 4/1989 | Marz et al. |
| 4,977,897 A | * | 12/1990 | Hurwitz ....................... 600/461 |
| 5,146,925 A | * | 9/1992 | Snow ........................... 600/435 |
| 5,196,015 A | | 3/1993 | Neubardt |
| 5,269,781 A | | 12/1993 | Hewell, III |
| 5,313,943 A | * | 5/1994 | Houser et al. ................ 600/374 |
| 5,433,708 A | * | 7/1995 | Nichols et al. ............... 604/113 |
| 5,474,558 A | | 12/1995 | Neubardt |
| 5,514,130 A | * | 5/1996 | Baker ............................. 606/41 |
| 5,520,189 A | * | 5/1996 | Malinowski et al. ......... 600/466 |
| 5,562,703 A | * | 10/1996 | Desai ............................ 606/210 |
| 5,775,331 A | | 7/1998 | Raymond et al. |
| 5,897,553 A | * | 4/1999 | Mulier et al. ................... 606/41 |

(Continued)

*Primary Examiner* — Max Hindenburg
*Assistant Examiner* — Sean Dougherty
(74) *Attorney, Agent, or Firm* — Koppel, Patrick, Heybl & Philpott; Michael J. Ram

(57) ABSTRACT

A device for use in a removing fluids and debris from a surgical wound and for location of nerves adjacent to the surgical wound comprises a hollow electrically conductive tube which has a lumen extending from the distal end thereof to the proximal end thereof. Openings are located at the distal end of the tube for suction removal of the fluid and debris. A handle located at the proximal end of the tube is provided for attachment of a second tube which is connected to a vacuum source. Also extending from or located within the handle is attachment means for connecting the conductive tube to an electrical nerve stimulation module. An electrically conductive ball is attached at the distal end of the conductive tube and distal to the openings in the tube. The openings are sized so that at least one dimension thereof is less then the diameter of the lumen to prevent the lumen from becoming clogged with debris having a size greater then the diameter of the lumen which is removed from the surgical wound.

7 Claims, 4 Drawing Sheets

U.S. PATENT DOCUMENTS

| | | | |
|---|---|---|---|
| 6,030,379 A * | 2/2000 | Panescu et al. | 606/34 |
| 6,149,620 A * | 11/2000 | Baker et al. | 604/22 |
| 6,234,178 B1 * | 5/2001 | Goble et al. | 128/898 |
| 6,358,248 B1 * | 3/2002 | Mulier et al. | 606/41 |
| 6,585,732 B2 * | 7/2003 | Mulier et al. | 606/41 |
| 6,682,501 B1 * | 1/2004 | Nelson et al. | 604/22 |
| 6,796,985 B2 | 9/2004 | Bolger et al. | |
| 6,837,884 B2 * | 1/2005 | Woloszko | 606/32 |
| 6,947,098 B2 | 9/2005 | Hentschel et al. | |
| 6,949,098 B2 | 9/2005 | Mulier et al. | |
| 7,186,234 B2 * | 3/2007 | Dahla et al. | 604/22 |
| 7,278,991 B2 * | 10/2007 | Morris et al. | 606/41 |
| RE40,156 E | 3/2008 | Sharps et al. | |
| 7,462,178 B2 * | 12/2008 | Woloszko et al. | 606/32 |
| 7,678,069 B1 * | 3/2010 | Baker et al. | 604/22 |
| 2002/0108614 A1 | 8/2002 | Schultz | |
| 2003/0014047 A1 * | 1/2003 | Woloszko et al. | 606/41 |
| 2003/0084907 A1 * | 5/2003 | Pacek et al. | 128/898 |
| 2004/0116922 A1 * | 6/2004 | Hovda et al. | 606/41 |
| 2005/0090816 A1 * | 4/2005 | McClurken et al. | 606/41 |
| 2005/0131402 A1 * | 6/2005 | Ciarrocca et al. | 606/41 |
| 2006/0189971 A1 * | 8/2006 | Tasto et al. | 606/32 |
| 2007/0015965 A1 * | 1/2007 | Cox et al. | 600/114 |

* cited by examiner

NERVE STIMULATOR WITH SUCTION CAPABILITY

This application claims benefit of Provisional Application No. 61/124,890 filed Apr. 21, 2008.

BACKGROUND OF INVENTION

Surgical procedures have historically utilized the application of electrical cautery to stop bleeding at the surgical incision as well as lower energy electrical pulses for nerve stimulation to locate nerves adjacent the surgical site. Electrically conductive instruments are touched to tissue at the surgical site, these instruments being attached to an electrocautery power source or a nerve stimulation pulse generator.

An insulated conductive suction device has been found useful for application of electrical energy to human patients for cautery. U.S. Pat. No. 6,947,098 shows an electrical cautery with a ball point roller like tip. It includes a central lumen for delivering a fluid to openings near the roller ball tip. While it does not include a suction channel for removal of the fluid or smoke from the tissue ablation procedure, it is indicated that suction channels shown in other patents, such as U.S. Pat. No. 5,269,781, can be added. US RE 40,156 is an example of an electric ablation device for destroying intervertebral discs. The device may also include lumens for delivering fluids to wash away debris created by the ablation and a suction channel for removing the fluid and debris. However, such a device would not be suitable for nerve stimulation along the walls of a hole drilled in the pedicle to locate adjacent nerves. Often the energy source wire is merely clipped to the instrument. Inclusion of a terminal for attachment of the stimulating or cautery lead wire more permanently to the instrument provides a more reliably and quantitatively verified delivery of the electrical energy.

U.S. Pat. No. 5,775,331 describes a device for electrical stimulation to locate a nerve and also indicates the device may include a suction channel for removing fluids. A major problem of present designs of suction cauterys or nerve stimulators with suction capability is that the lumen of the suction device can become repeatedly blocked and clogged by bone chips or tissue when applied to a freshly drilled hole in bone. In addition, the open tip of the presently available open-end suction tube designs poses a risk of trauma to fragile nervous and vascular structures from the direct application of suction.

Under certain circumstances a medically desirable procedure is the stabilization or fusion of a portion of the spine to prevent motion. For example, the spine may be stabilized after a decompression procedure where certain posterior spinal elements are removed to relieve pressure on nerves within the spine. It may also be necessary to stabilize or fuse the spine following trauma or the removal of tumors. As part of those procedures pedicle screws are inserted in selected vertebrae to hold stiff rods or plates between adjacent pedicles, resulting in the fixing or bracing of all vertebrae spanned by the rod or plate. The pedicle screws are usually made of stainless steel and typically have thread outer diameters from about 5.5 mm to about 6.5 mm, and lengths between about 25 mm to 55 mm. One of the major causes of unsuccessful back surgery is the proximity of the screw to one or more nerves within the spine or pedicle creating chronic pain.

Because the pedicles are the strongest parts of the spinal vertebrae this arrangement provides a secure foundation for the attached rods or plates. However, maximum mechanical integrity is obtained when the anchoring pedicle screws are threaded in alignment with the pedicle axis. If they are allowed to deviate off axis the screw body or its threads can break through the vertebral cortex and impinge on or become dangerously close to surrounding nerve roots. Slight deviations in the angle of screw insertion can injure the nerve roots or the spinal cord. Even if the pedicle screw is properly aligned it may be placed to close to a nerve, resulting in chronic, postoperative pain. There are numerous articles in the literature regarding the problems of misalignment of pedicle screws and the symptoms arising when the screws make contact with neural elements after breaking outside the pedicle cortex. Cutting into a nerve root or simply contacting the root gives rise to various postoperative symptoms such as dropped foot, neurological lesions, sensory deficits, or pain. (The Adult Spine—Principles and Practice, Vol. II, at pages 1937 and 2035-36 (Raven Press 1991); J. L. West, et al, Complications of the Variable Screw Plate Pedicle Screw Fixation, Spine (May 1991), at pages 576-79; and J. L. West, et al, Results of Spinal Arthrodesis with Pedicle Screw-Plate Fixation, Journal of Bone and Joint Surgery (September 1991), at pages 1182-83.)

While there are various disclosures of devices designed to properly align the screws, no tools or devices are known with which pedicle screws can be guided or inserted into a vertebra in such a manner as to ensure that the screws do not come unnecessarily close to adjacent nerves. The surgeon may use recognized landmarks along the spinal column for purposes of locating pedicle entry points and X-rays or fluoroscopy to monitor the advancement of a metallic pedicle screw through the vertebra. However, prolonged exposure of the patient to X-rays for purposes of proper screw placement is not desirable and this technique can still result in an unacceptable level of pedicle screw placement.

It is also generally known that electrical potential pulses may be applied on or into the body of a patient for purposes of treatment. For example, U.S. Pat. No. 4,461,300 (Jul. 24, 1984) discloses a specially formed electrode for healing of bone or soft tissue fractures in a patient. The electrode has a lead wire connected at its back end, and is capable of being drilled or otherwise inserted into the patient's body with the lead wire in place.

An alternative technique is to monitor muscular response to electrical stimulation during a screw placement procedure or the drilling of a hole to receive the screw. U.S. Pat. No. 2,808,826 shows electro-diagnostic apparatus and associated circuitry that act as a stimulator to measure the excitability of muscle or nerve tissue. A pair of electrodes are placed across a part of the patient's body and short duration pulses are applied with the pulse amplitude being slowly increased until a visible contraction appears. Electrical current readings are obtained for pulses of increasing duration, and a curve called a "strength-duration" curve is obtained.

U.S. Pat. No. 4,824,433 discloses a puncturing and catheterizing device with a metal puncture needle and cannula suitable for puncturing nerve tracts. Pulses of electrical current applied to the device induce visible motor reactions on body parts such as the hand. The visible muscle responses or responses detected by suitable electronic metering devices allow the physician to know if the current delivery electrode is undesirably close to a nerve.

One skilled in the art is familiar with nerve stimulation electrodes and systems such as are typically used in motor nerve location and monitoring procedures performed during various medical procedures such as thyroidectomy, anterior cervical fusion, craniotomy, skull base procedures, carotid endarterectomy. Typical procedures where nerve location is beneficial is EMG nerve location, locating and monitoring the recurrent laryngeal nerve, xth cranial nerve and other nerves using laryngeal surface electrodes and surface electromyography to preserve vocal cord function and prevent vocal cord injury. The technology is typically used by ear, nose and throat doctors (ENT, otolaryngologists), orthopedic surgeons and general surgeons in otologic and neck procedures, particularly in thyroidectomy, parathyroidectomy and paratoidectomy procedures.

U.S. Pat. Nos. 5,196,015 and 5,474,558 to Seth Neubardt describe a technique of inserting a screw member into bone tissue of a patient following the formation of a hole for screw placement. The technique describes the application of an electric potential to the interior surface of the hole while observing the patient for nervous reactions to the electric potential. To do so an electric potential is applied to a drill bit used to form the opening in bone tissue for insertion of a screw member, and the response of adjacent nerves is observed during the hole forming procedure.

U.S. Pat. No. 6,796,985 to Bolger, et al. is another patent directed to a neurostimulator attached to the drilling tool.

As an alternative, the holes are drilled with standard orthopedic instruments, the drilled holes are cleaned of fluid and bone debris, and a needle probe attached to a nerve stimulation device is placed in the hole to determine if there are nerve ends adjacent the walls or terminus of the hole such that a screw inserted in the hole will interact with adjacent nerves to cause post surgical pain. Presently, the suction cleaning of the drilled hole and subsequent nerve location are done using separate suction devices and nerve stimulators. This results in inconsistent results as the hole can fill with blood or other fluids after removal of the suction devices; the detection or measurement of the electrical signal conducted between the stimulator tip and the adjacent nerve can then vary due to the time delay between suctioning the hole and applying the nerve stimulation device, or the amount of fluid within the opening.

SUMMARY

A single device providing the ability to suction fluid and debris from a surgical wound and apply an electrical charge for location of nerves adjacent to the surgical site comprises a hollow electrically conductive tube having a lumen extending from the distal end thereof to the proximal end thereof. Openings pierce the wall of the tube at the distal end thereof for suction removal therethrough of the fluid and debris. Structure at the proximal end thereof provides for attachment of a tube connected to a vacuum source and collection canister. An electrically conductive ball attached to the conductive tube distal to the openings at the distal end of the conductive tube allows the device operator, immediately following cleaning of the surgical wound, to explore all of the surfaces of the wound to determine the proximity of adjacent nerves. The one or more openings at the distal end of the tube have a smallest dimension less then the diameter of the lumen to prevent the lumen from clogging with debris removed from the surgical wound. The suction/nerve stimulator has particular utility in locating nerves adjacent the walls or apex of a hole drilled in the spinal pedicle to receive a screw to affix structures for stabilization or fusing of the spine.

DETAILED DESCRIPTION

The present invention is the first device to address the inadequacy of the use of separate suction tools and stimulator needles and to provide consistent nerve stimulation/location so as to minimize screw/nerve interaction.

The present invention is directed to a metallic, electrically conductive suction tube that includes a pin for attaching the leads from an electrical pulse generator to provide a controlled electrical output for us in stimulating nerves. The tube is coated with an insulating material such as Teflon or other electrical insulator coatings so that stimulation is delivered only to the tip of the device. The tip of the suction device is closed and has a metallic conductor ball attached for stimulating purposes in electrical continuity to the connecting pin and stimulator lead wire, for nerve stimulation. The wall of the suction tube nearest where it is attached to the ball has one or more openings, preferable two or more openings, cut therein, so as to form a cruciate opening to provide an inlet for air, fluid and debris to be drawn by suction into the lumen of the tube. The inlets are preferably shaped and sized so that bone chips will not adhere to the outer surface of the inlets, by the force of suction, but will be able to enter into the main channel of the suction tube. The size of the openings is chosen to be smaller in cross sectional size so that debris passing through the opening and entering the tube will have a diameter smaller than the tube inner diameter so as not to obstruct the suction flow. The ball shape of the tip is chosen to allow for sidewall stimulation of a freshly drilled hole by a "ball-tip" stimulation probe while preventing bone chips and other soft tissue structures from clogging the suction tube as well as providing an atraumatic application of both suction and stimulation.

Figure 1:
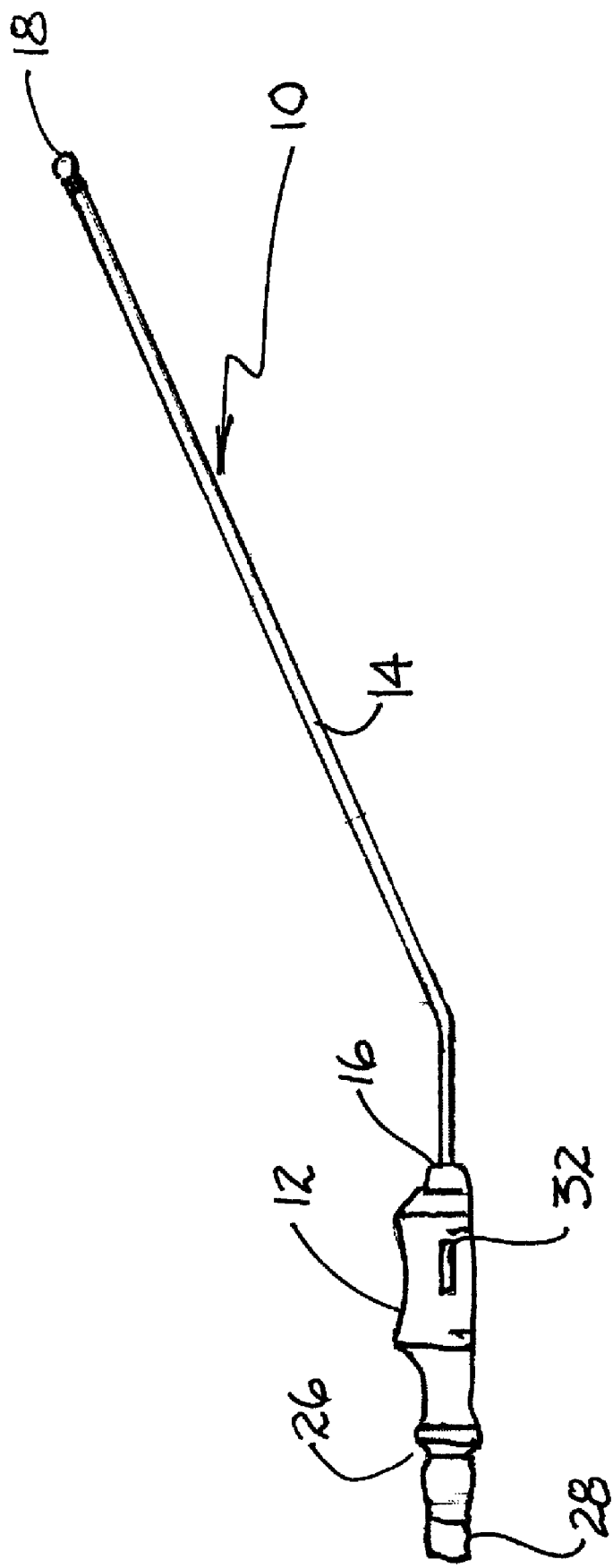
FIG. 1 is a side view of a device incorporating features of the invention.
Figure 3:
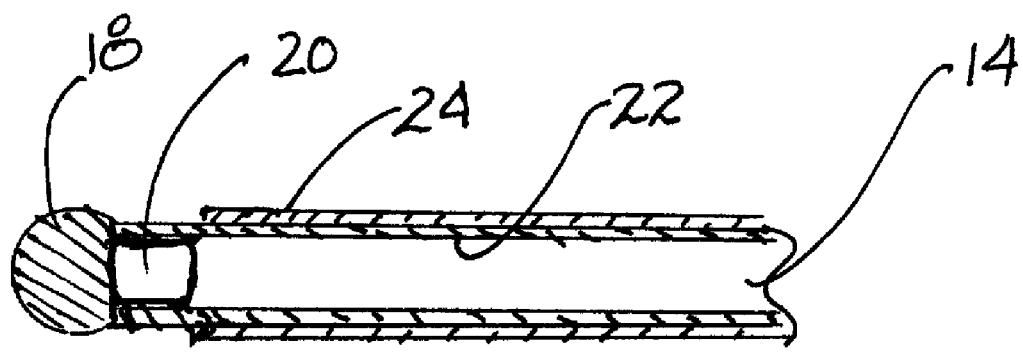
FIG. 3 is an enlarged cutaway top view of the tip portion of the device of FIG. 1.
Figure 5:
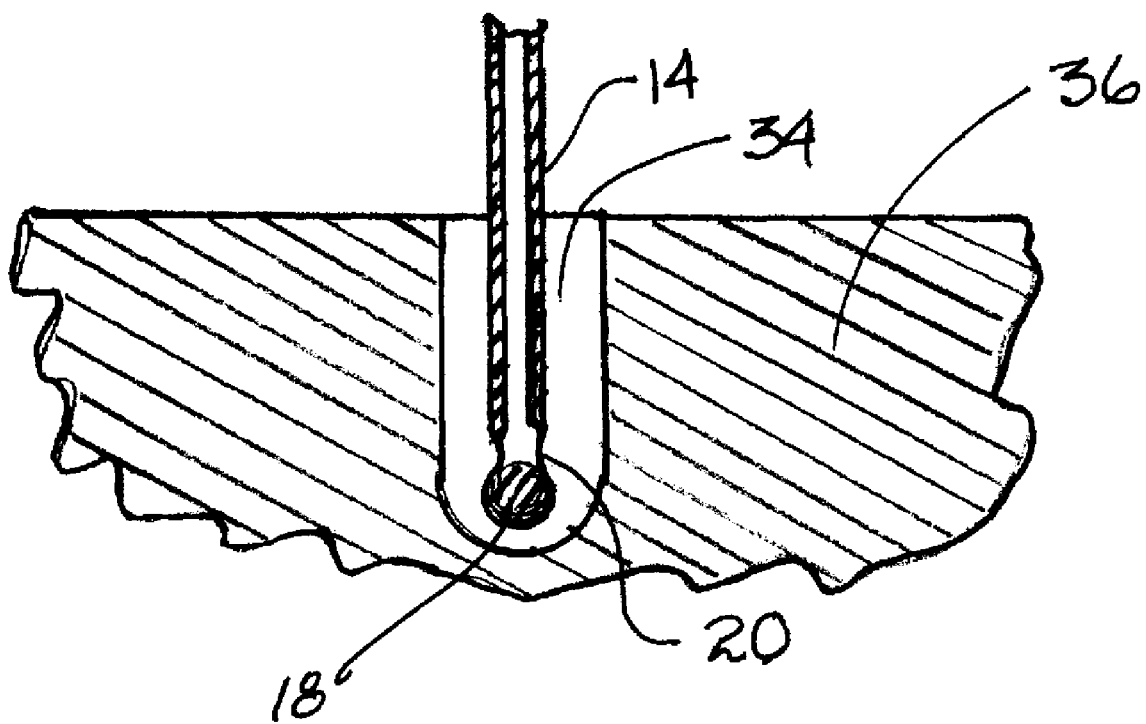
FIG. 5 is a cutaway section through a portion of bone showing the device of claim 1, also cut-away, inserted in a drilled hole prior to placement of a screw.

Referring to the drawings, FIG. 1 shows a suction/nerve stimulator 10 incorporating features of the invention comprising a connection handle 12 with a hollow, tubular extension 14 attached to a forward end 16 of the handle. The distal end of the extension has a ball tip 18 formed there on or welded thereto and, adjacent to the ball tip 18, one or more openings 20, also referred to as suction ports. The diameter of the ball tip 18 is preferably equal to or greater than the outer diameter of the extension 14 so that contact with the walls can be easily made. The tubular extension 14 may be provided in various different lengths the length not being critical, as best suited for the medical procedure to be performed. The ball tip 18 of the suction/nerve stimulator 10, further discussed below, is best shown in FIGS. 3 and 5. The ball tip 18 and the inner tube 22 of the tubular extension 14 are formed from an electrically conductive material, such as steel. A non-conductive, insulating coating 24 provides an outer barrier over the inner tube 22 of the extension 14.

Figure 2:
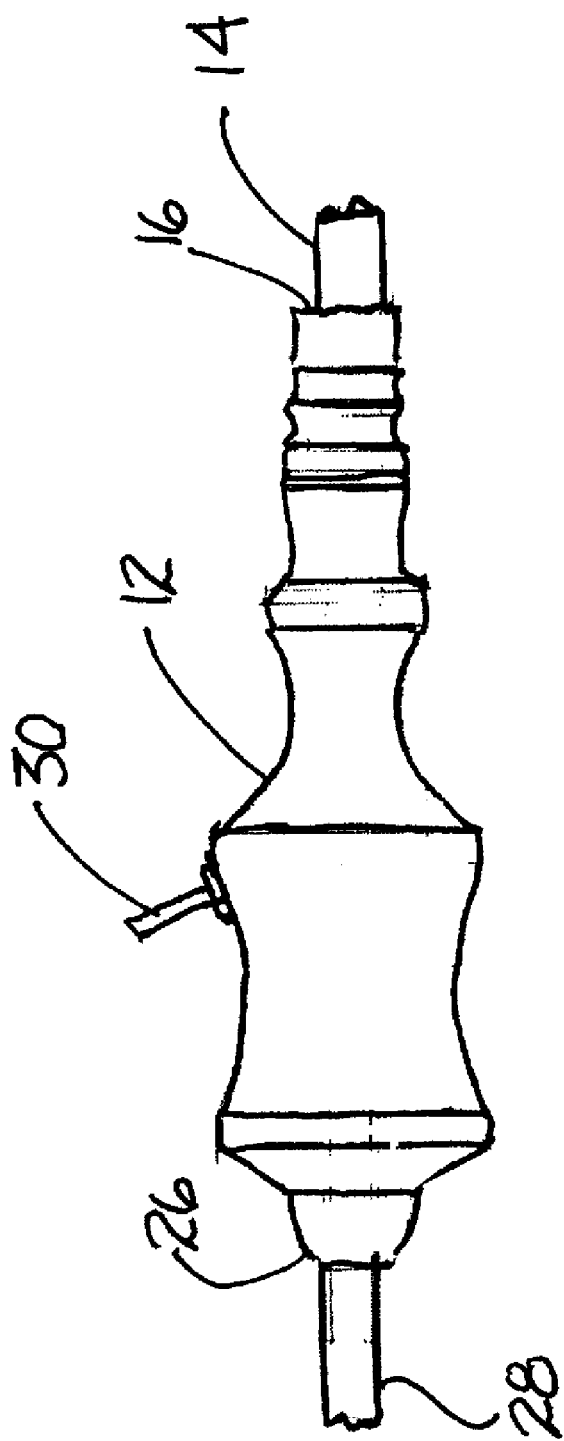
FIG. 2 is an enlarged top view of the handle portion of the device of FIG. 1.

The connection handle 12, as best shown in shown in FIG. 2, is a hollow structure also formed of a compatible electrically conductive material and is covered with the same insulating material. The extension tube 14 is seen projecting out of a forward end 16 of the connector 12. The rear or proximal end 26 of the connector 12 is configured for attachment of a standard suction line 28, which is typically a flexible rubber of polymeric material. Projecting from a middle portion of the connector 12 is an electrically conductive pin 30 for attachment of an electrical lead from a electrical stimulation signal generator (not shown) such that an electrical lead applied to the conductive pin 30 provides an electrical current feed through the conductive connection handle 12, the inner tube 22 of the extension 14 and the ball tip 18 and delivered to a site within a surgical opening in a medical procedure as described below. Alternatively, the conductive pin 30 can be replaced by an opening in the connector 12 for inserting of a electrical jack or plug for transmission of an electrical signal into the conductive tube. Means are also provided on, in or operative with the connection handle 12 to control the levels of suction. FIG. 1 shows a hole 32 that connects with the suction channel in the connection handle 12. The level of suction, or on/off suction control, can be provided by the operator partially or fully occluding the hole with a finger. Alternatively, an adjustable valve can be provided on or in the connection handle 12, the tubular extension 14 or the suction line 28 or on the suction delivery system. US Published Patent Application 2002/0108614, incorporated herein in its entirety, shows several different suction device handles which include structures for controlling or adjusting the level of suction. One skilled in the art can readily select suitable suction control means.

A ball shaped tip 18 is preferred for general procedures as this allows for a uniform delivery of the electrical signal over the tip surface and the ability to contact all surfaces in the drilled hole. Generally a tip with sharp edges or points is not desired as this construction tends to focus the electrical charge to the sharp edge or point and may deliver a greater charge to the tissue then desired. However, special devices which include different shapes other then the ball tip, for example a pyramid shaped tip or a needle like projection can be provided in place of the ball tip 18 for specialized procedures.

Figure 4:
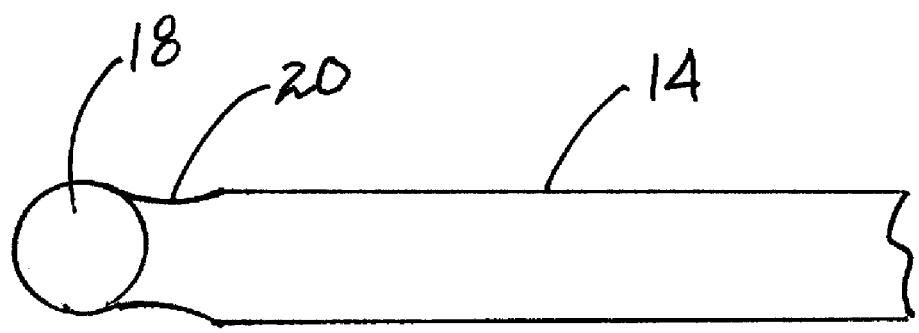
FIG. 4 is an enlarged side view of the tip portion of the device of FIG. 1.

The suction ports 20 are sized so that at least one dimension, such as the width, as best shown in FIG. 4, is smaller than the lumen of the extension tube or any opening down stream thereof As a result, solid debris, such as bone chips, and tissue which passes through the opening of the suction port 20 will not clog or block the lumen of the extension tube, the hollow within the connection handle 12 or the suction line 28. The suction ports 20 also preferably do not have any sharp edges or extensions which could trap debris or bone chips on the surface thereof. FIGS. 3 and 4 show two suction ports 20, but a single port or more then two ports can be used. Further, the ports are shown as elongated ovals but other shaped openings or slits can be used as long as they do not depart from the general teachings herein.

To use the device described herein for pedicle screw placement one or more holes 34 are formed in the pedicle 36, the ball tip is placed in the hole 34, suction is drawn to remove any fluid and debris in the hole 34 and a stimulating electrical signal is applied to the ball tip 18. One unique aspect of the invention is that the ball-shaped tip allows the electrical signal to be applied selectively to any and all of the internal surfaces of the hole to determine if the hole is to close to a nerve such that placement of a screw in that hole will create a pain-eliciting response in an adjacent nerve. Use of a straight needle-shaped electrode allows contact with the apex of the drilled hole but does not provide capability for exploring the walls of the cavity. The cavity walls can only be adequately explored by using a second needle electrode with a bent tip and, unlike the ball tipped electrode must be rotated to bring the tip into contact with all of the wall surfaces. Exploration of all of the wall surfaces using the ball tip can be accomplished merely by drawing the probe up and down while in contact with the desired portion of the wall.

I claim:

1. A device for use in removing fluids and debris from a surgical wound and for location of nerves adjacent to the surgical wound by providing a suitable nerve stimulating electrical output comprising a hollow electrically conductive tube having a lumen of a predetermined diameter extending from a distal end thereof to a proximal end thereof, openings at the distal end thereof for suction removal therethrough of the fluid and debris, structure at the proximal end thereof for attachment of a second tube connected to a vacuum source, and an electrically conductive ball attached to the conductive tube distal to the openings at the distal end of the conductive tube the openings having at least one dimension less than the diameter of the lumen to prevent the lumen from clogging with debris removed from the surgical wound having a size greater than the diameter of the lumen.

2. The device of claim 1 wherein the hollow electrically conductive tube has an outer surface with an electrically non-conductive coating over the entire outer surface.

3. The device of claim 1 further including a connection handle affixed to the proximal end of the hollow electrically conductive tube, the connection handle including a electrically non-conductive surface, structure at the proximal end thereof for attachment of a tube connected to a vacuum source, suction control means being located on or in said connection handle, and an electrically conductive extension for connection to a nerve stimulating electrical source.

4. A device for use as part of a procedure for the placement of pedicle screws comprising, in combination, a suction device and an electrical nerve stimulator, the device comprising an electrically conductive tube, said tube having a ball shaped tip on a distal end thereof, one or more suction openings in a wall of the tube just proximal of the ball shaped tip and a lumen of a predetermined diameter extending from said one or more suction openings to a handle at a proximal end of said tube.

5. The device of claim 4 wherein said electrically conductive tube and the handle have an outer surface and the outer surface of the tube and the handle, but not the ball shaped tip, have an electrically non-conductive coating covering the outer surface thereof.

6. The device of claim 5 wherein an electrical connector is provided on or in the handle for attachment of the electrically conductive tube to a source of electrical stimulation and the handle includes a suction port for providing a connection between the lumen in the tube and a vacuum source.

7. The device of claim 4 wherein the one or more suction openings are each sized to prevent flow therethrough of debris with a dimension larger than the diameter of the lumen in the tube.

* * * * *